United States Patent [19]
Yoshida et al.

[11] Patent Number: 5,460,968
[45] Date of Patent: Oct. 24, 1995

[54] ANALYTICAL METHOD AND ANALYTICAL APPARATUS USING TEST STRIPS

[75] Inventors: Kasumi Yoshida, Mito; Isao Shindo, Katsuta; Susumu Kai, Katsuta; Yutaka Kimura, Katsuta, all of Japan

[73] Assignee: Hitachi, Ltd., Tokyo, Japan

[21] Appl. No.: 348,210

[22] Filed: Nov. 28, 1994

Related U.S. Application Data

[63] Continuation of Ser. No. 962,820, Oct. 19, 1992, abandoned.

[30]  Foreign Application Priority Data

Oct. 21, 1991  [JP]  Japan .................................. 3-272322

[51] Int. Cl.$^6$ .................................................. G01N 35/02
[52] U.S. Cl. ................... 436/46; 436/47; 436/48; 422/62; 422/63; 422/82.06
[58] Field of Search ............... 422/62–66, 82.05, 422/82.06; 436/46–48

[56]  References Cited

U.S. PATENT DOCUMENTS 4,451,433  5/1984  Yamashita et al. ..................... 422/63
4,578,588  3/1986  Galkin ................................. 250/432 R
4,876,204  10/1989  Inoue et al. ............................. 422/63

FOREIGN PATENT DOCUMENTS 180792    5/1986  European Pat. Off. .
3241922   5/1984  Germany .
61-91571  5/1986  Japan .

Primary Examiner—Lyle A. Alexander
Attorney, Agent, or Firm—Fay, Sharpe, Beall, Fagan, Minnich & McKee

[57]  ABSTRACT

A sample container containing a urine sample is transferred by a sample positioning device to a liquid level sensing position. At this sensing position, the liquid level in the sample container is detected by a level sensor, followed by transfer of the sample container to a dipping position. A liquid level rising member is then inserted into the sample container. While being held by a handling device, a test strip is dipped into the sample in the sample container with the liquid level raised. Thereafter, the test strip is lifted out of the sample container and transferred to a measuring device. Color development in reagent sections on the test strip is measured by a photometer in terms of the reflected light strength. With the present invention, analysis using test strips can be implemented even when the sample volume into the sample container is small.

17 Claims, 4 Drawing Sheets

FIG. 3A
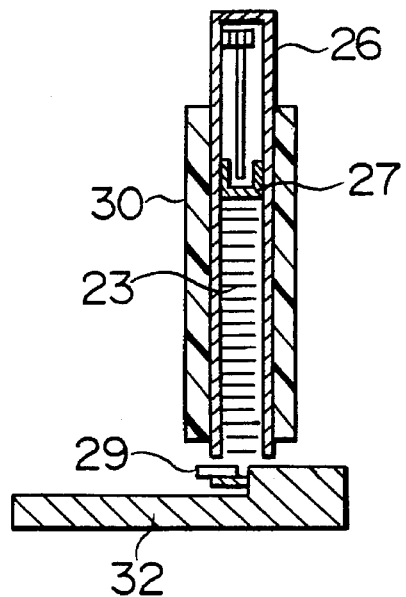
FIG. 3B
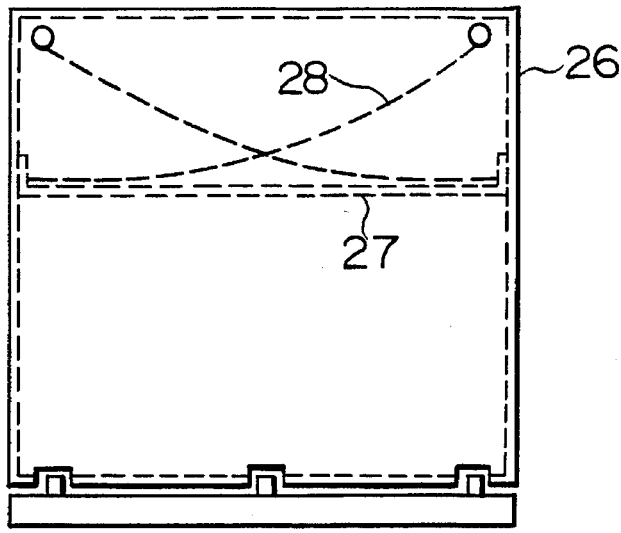
FIG. 4A  FIG. 4B  FIG. 4C
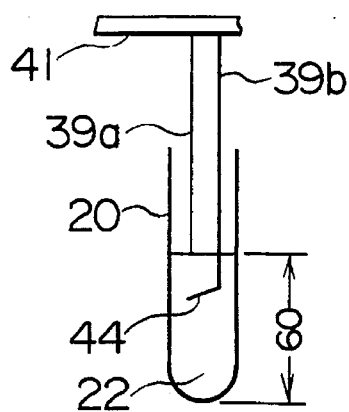
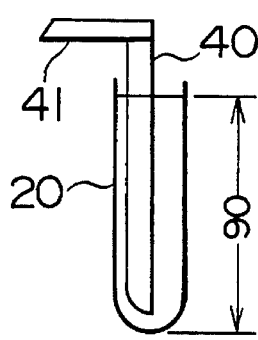
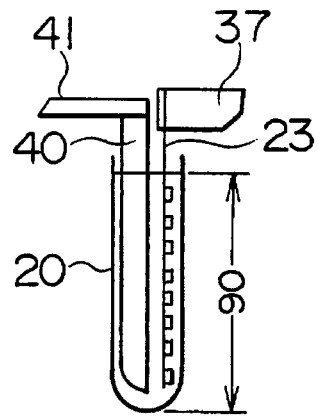

ANALYTICAL METHOD AND ANALYTICAL APPARATUS USING TEST STRIPS

This is a continuation application of Ser. No. 07/962,820, filed Oct. 19, 1992, now abandoned.

BACKGROUND INVENTION

1. Field of the Invention

The present invention relates to an analytical method and an analytical apparatus using test strips, and more particularly to an analytical method and an analytical apparatus in which a biological sample such as urine or blood is caused to develop a color reaction in reagent sections on test strips.

2. Description of the Prior Art

A method of analyzing using test strips, each of which is made by impregnating small strips of felt or the like with reagents to form a plurality of reagent sections or test sections, and then by bonding the small strips to a plastic stick, has been adopted, for example, in a screening test for group examination and diagnosis of diseases. An apparatus capable of automatically carrying out operations necessary for such a method is disclosed in Japanese patent unexamined publication 61-91571. Note that this Japanese patent unexamined publication corresponds to U.S. Pat. No. 4,876,204.

In the analytical apparatus disclosed in the above-cited Japanese patent unexamined publication 61-91571, a test strip supplied from an automatic supply device is held by a handling device, and the test strip is dipped into a sample liquid in a sample container. After that, the test strip is lifted out of the sample container and transferred to a reaction table. The test strip is then transported to a light detecting portion where colored reagent sections are measured.

This reference also discloses an arrangement for measuring a sample liquid level in the sample container and giving an advance notice of insufficiency of the sample liquid, prior to dipping the test strip into the sample liquid. Further, an arrangement for detecting the liquid level in bottles is disclosed in U.S. Pat. No. 4,451,433, by which the liquid level of reagent solutions supplied to a chemical analyzer is detected by a pair of electrodes.

In the apparatus of the above-cited Japanese patent unexamined publication 61-91571, those samples of whose volumes are insufficient for thorough immersion of the reagent sections of the test strip are all disabled from measuring and, therefore, automatic measurement cannot be achieved. More specifically, the test strip comprises a plastic stick having a plurality of reagent sections arranged in the direction of stick length. To make all the reagent sections thoroughly dipped in a sample, it is required that a sufficient volume of sample has been sampled in the sample container. In the practical working field, however, samples are occasionally used having sample volumes that are too small to provide a sufficient liquid depth in the sample containers.

SUMMARY OF THE INVENTION

An object of the present invention is to provide an analytical method and an analytical apparatus by which multi-item analysis can be performed using test strips even when the volume of a sample liquid contained in a sample container is not sufficient.

According to the present invention, there is provided an analytical method using test strips, each of which has reagent sections able to develop colors upon contact with a sample, for example upon being dipped into a sample liquid in a sample container, the reagent sections being then subjected to optical measurement, wherein the sample container is reduced in sectional area and in its effective volume to contain the sample liquid, thereby raising a surface level of the sample liquid, so that the test strip can be dipped into the sample liquid while a sufficient sample liquid level is maintained.

BRIEF DESCRIPTION OF THE DRAWINGS

FIG. 2A is a plan view and FIG. 2B is an elevational view.

FIGS. 3A and 3B show a structural example of a cassette in which test strips are stored; FIG. 3A is a vertical sectional view and FIG. 3B is a front view.

FIGS. 4A, 4B and 4C show a principal part of the analyzer shown in FIG. 1 and are illustrations for explaining successive operation steps of a sample liquid level adjustable device.

DETAILED DESCRIPTION OF THE PREFERRED EMBODIMENTS

A sample container is supplied with a sample liquid contained therein. A test strip has a plurality of reagent sections arranged in series thereon corresponding to multiple analytical items. The volume of the sample liquid necessary to ensure that all the reagent sections are thoroughly immersed in the sample liquid is related to the depth and sectional area of the sample container, as well as the depth by which the test strip is inserted in the sample container.

For convenience of description, the surface level of the sample liquid at which all the reagent sections can be thoroughly immersed into the sample liquid will be referred to as a reference level. The reference level is related to the bottom of a sample-containing chamber of the sample container and a level position adapted to completely cover the uppermost reagent section when the inserted test strip is maximally lowered. In general, the distance between the bottom of the sample-containing chamber of the sample container and the lower end of the test strip suspended from handling means during the immersion is always kept constant. When the sample liquid level in the sample container prior to immersion of the test strip does not reach the reference level, it is difficult to bring all the reagent sections into contact with the sample liquid. To cope with this difficulty, therefore, the test strip is dipped after raising the sample liquid level in the sample container.

In order to raise the sample liquid level, a liquid level rising member for reducing the sectional area, and thus the effective volume, of the sample container itself is inserted into the sample container. This liquid level rising member preferably comprises a rod-like member having an outer configuration a part of which conforms to the shape of an inner wall of the sample container. Further, the liquid level rising member, which is to be supported in a vertically movable manner, is designed position thereof and the inserted position thereof so that when the liquid level rising member is immersed the insertion of the test strip into the sample container will not be prevented. When the liquid level rising member is lowered to enter the sample liquid, the sample liquid level in the sample container is raised depending on the liquid displacement of the liquid level rising member that has entered the sample liquid. When the sample liquid level is equal to or higher than the reference level, the test strip is dipped into the sample liquid. All the reagent sections can thereby be contacted with the sample liquid for the same period of time, making it possible to have uniform start conditions for color developing reactions in the various reagent sections.

Figure 1:
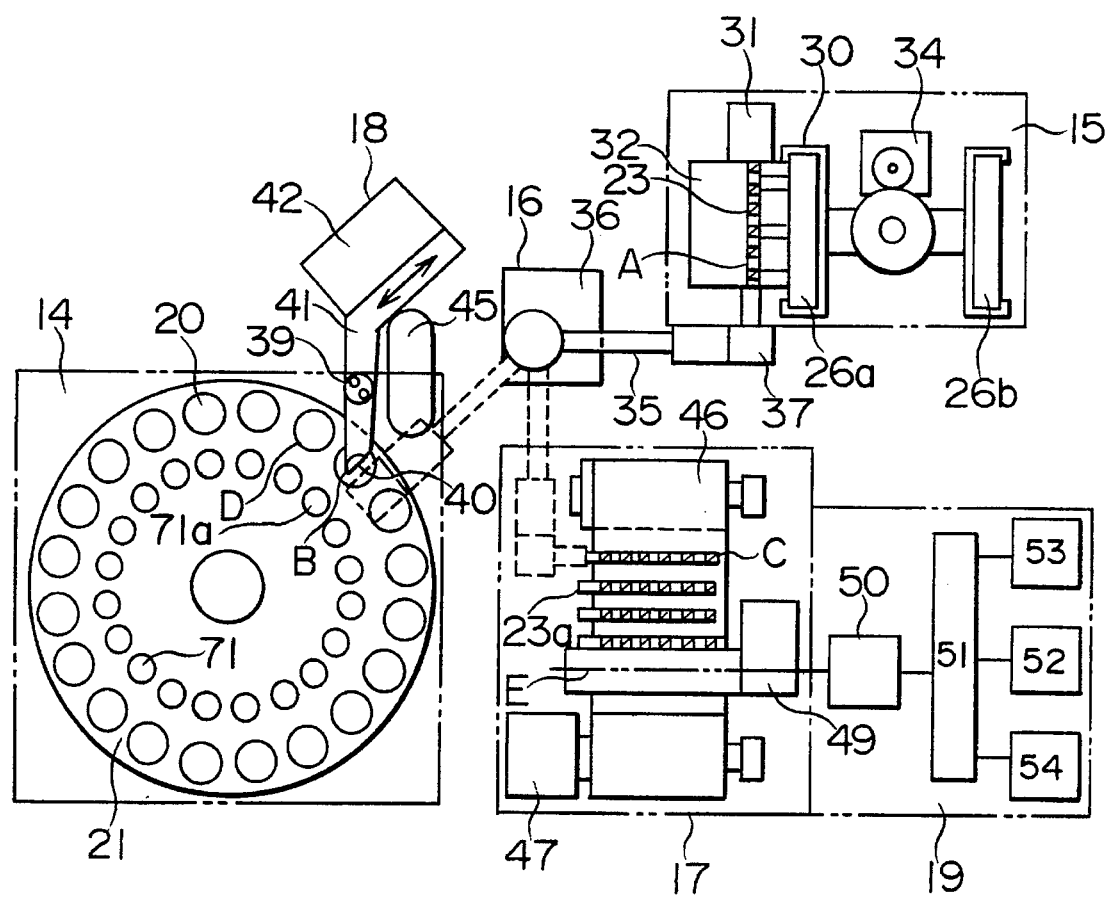
FIG. 1 is a schematic view showing the overall construction of a urine analyzer to which the present invention is applied.

The urine analyzer shown in FIG. 1 comprises a sample positioning device 14, a test strip automatic supply device 15, a test strip handling device 16, a liquid level adjustable device 18, a measuring device 17, and a control and data processing device 19. The sample positioning device 14 includes a plurality of sample containers, each containing a sample liquid, arranged thereon and operates to successively transfer and position the sample containers to a test strip dipping position. The test strip automatic supply device 15 accommodates a plurality of test strips and operates to deliver the test strips one by one to a pick-up position. The test strip handling device 16 grasps the delivered test strip, dips it into the sample liquid in the sample container held at the immersion position, and thereafter transfers the same to a test strip setting position in, the measuring device 17. In the measuring device 17, the set test strip is transferred to a measuring position to conduct a measurement. When dipping the test strip into the sample liquid, if the sample liquid level in the sample container is lower than the reference level at which the portion of the test strip that contributes to reactions for analysis of the test strip can thoroughly be immersed in the sample liquid, the liquid level adjustable device 18 inserts a liquid level rising member or rod 40 into the sample container to such an extent that the sample liquid level is raised up to the predetermined or reference level.

In a preferred embodiment of the present invention, the liquid level adjustable device 18 includes a liquid level sensor. The liquid level sensor may be of the type that electrodes are inserted into the sample container to detect contact of the electrodes with the liquid surface, or the type that the liquid level is optically detected from the outside of the sample container. Control of the extent by which the liquid level rising member is inserted into the sample container, and the operation of dipping the test strip into the sample container by the test strip handling device 16 are performed by one of the following first and second methods, or a combination of the two.

With the first method, the sample liquid level is measured before the liquid level rising member is inserted into the sample container. More specifically, prior to insertion of the liquid level rising member into the sample container, the liquid level sensor of the electrode type is inserted into the sample container for measuring the sample volume or the sample liquid level in the sample container. Based on the measurement result, the control and data processing device 19 calculates and determines the extent of insertion of the liquid level rising member which is necessary for raising the sample liquid level in the sample container up to the predetermined level. Then, the sample liquid level adjustable device is operated to insert the liquid level rising member into the sample container so that the sample liquid level in the sample container is raised up to the predetermined level, i.e. enough to make the test strip thoroughly immersed into the sample container. After that, the test strip handling device is operated to dip the test strip into the sample liquid in the sample container.

With the second method, the sample liquid level in the sample container is detected while inserting the liquid level rising member into the sample container. In this case, the liquid level sensor is set beforehand at a desired level position. When the liquid level is raised to reach the sensor position, that liquid level is detected, whereupon the operation of inserting the liquid level rising member is stopped. Specifically, after setting of the sensor, the liquid level adjustable device is operated to insert the liquid level rising member into the sample container, thereby raising the sample liquid level in the sample container up to the position detectable by the sensor. In this state, the sample liquid level reaches the predetermined level necessary for immersing the test strip in the sample liquid. Thereafter, the test strip is dipped into the sample liquid in the sample container.

As the liquid level rising member, there is used a rod-like member formed such that the portion which is inserted into the sample container has a length at least ½ of, preferably almost equal to, the length of the sample container, and the main portion which is dipped into the sample liquid has a sectional area at least ⅕ preferably ⅓ or more, in terms of the inner diameter of the sample container. The liquid level rising member is configured and located in relation to the sample container so that the insertion of the test strip into the sample container will not be prevented.

FIG. 1 shows a structural view of an automatic urine analyzer to which the present invention is applied. In the sample positioning device 14, a plurality of sample containers 20 each containing a urine sample to be analyzed are arranged on a turntable 21. The turntable 21 is turned at predetermined time intervals for successively transferring the sample containers 20 to a test strip dipping position B. The number of the sample containers allowed to be loaded on the turntable 21 is 60 in the illustrated embodiment. The test strip automatic supply device 15 has a function to supply test strips 23, which are stored beforehand in place, one by one to a pick-up position A in synchronism with the analytical cycle.

Figure 2A:
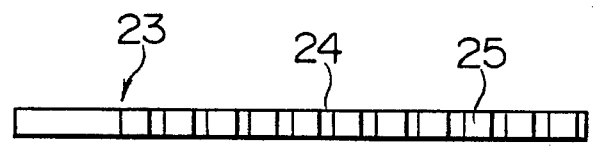
FIGS. 2A and 2B show an example of a test strip.
Figure 2B:
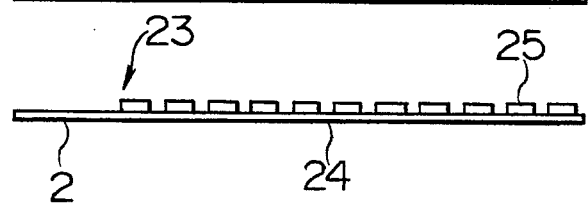

As shown in FIG. 2, the test strip 23 comprises a rectangular stick plate or stick 24 on which a plurality of reagent sections (or test sections) are arranged in the direction of stick length. The reagent sections respectively correspond to individual analytical items.

The test strip 23 has a grip region 2 at one end side. Each reagent section 25 is formed of a small strip of filter paper or felt impregnated with a reagent corresponding to the analytical item.

In the example shown in FIG. 2, the test strip includes eleven small strips in total; namely ten reagent sections subjected to analysis and one standard section for color compensation. The test strip has an overall length of about 120 mm and the total length of the reagent sections is about 90 mm. To immerse all of the reagent sections thoroughly into the sample liquid, therefore, the sample liquid in the sample container is required to have a liquid level not lower than 90 mm. The sample container usually employed in urine analysis is approximately 100 mm long.

FIGS. 3A and 3B show the structure of a test strip cassette 26 storing the test strips 23 therein. The test strips 23 are stored in the cassette 26 such that they are pressed toward a take-out port 29 by a leaf spring 28 via a retainer plate 27. The cassette 26 is mounted to a cassette holder 30 of the test strip automatic supply device 15, and a test strip delivery device 32 operated by a motor 31 delivers the test strips one by one to the pick-up position A. The test strip automatic supply device 15 includes two units of cassettes 26 each capable of storing 100 test strips 23. When one cassette 26a is exhausted, a cassette change-over device 34 is turned to automatically replace it with the other new cassette 26b.

The test strip handling device 16 shown in FIG. 1 includes a drive mechanism 36 for causing an arm 35 to move vertically and to swing or rotate about a vertical shaft, and a test strip gripper (or a grip) 37 attached to the distal end of the arm 35 to detachably hold the test strip 23 and rotate about an axis. The test strip handling device 16 grasps the test strip 23 in the pick-up position A, dips it into the sample liquid in the sample container 20 positioned in the dipping position B, lifts it out of the sample liquid after a predetermined period of time, transfers it to a test strip setting position C in the measuring device 17, and releases it from the grasped state.

In the liquid level adjustable device 18 shown in FIG. 1, a pair of liquid level sensing electrodes 39a, 39b and the liquid level rising member 40 are supported by the arm 41 to be suspended therefrom (see FIG. 4). The arm 41 is operated by a drive mechanism 42 so that it moves horizontally (in directions of the arrows in FIG. 1) and vertically.

The operation of adjusting the sample liquid level will now be described with reference to FIGS. 1 and 4. In the turntable 21, there are provided holes 71 into which the sample containers 20 are to be loaded. When the arm 41 is advanced toward the turntable 21 in the direction of one arrow in FIG. 1 and the liquid level sensing electrodes 39 are positioned at a detection position D, the liquid level rising rod (or member) 40 is located just above the hole at a position 71a. Upon lowering the arm 41, the electrodes 39 are lowered to enter the sample container in the detection position D, while the member 40 is lowered to penetrate through the hole at the position 71a. When the arm 41 is retracted in the opposite direction, the rod 40 and the electrodes 39 are positioned in a state as shown in FIG. 1. When the arm 41 is further retracted outwardly, the member 40 and the electrodes 39 are positioned above a washing tank 45.

More specifically, while the liquid level adjustable device 18 is in a standby state, the member 40 and the electrodes 39 are held above the washing tank 45. When the liquid level adjustable device 18 starts its operation, the arm 41 is advanced inwardly so that the electrodes 39 are positioned at the detection position D preceding one step from the dipping position B. Then, as the arm 41 is lowered, the electrodes 39a and 39b are caused to enter the sample container in the detection position D and are stopped at such a level position that both the electrodes are contacted with the sample liquid surface. One electrode may be contacted with the sample liquid surface while the other electrode is immersed in the sample liquid, as shown in FIG. 4a. The control and data processing device 19 determines whether the detected sample liquid level or sample volume reaches the necessary minimum level or amount. The necessary minimum level of the sample liquid surface is set beforehand as a fixed value depending on the adjustable capability of the liquid level rising member 40, and the set value is stored in a memory of a control unit 51.

It is set in the illustrated embodiment that the sample container has a length of 100 mm, the sample liquid level necessary for thoroughly immersing the test strip into the sample liquid is 90 mm, and further the minimum sample liquid level required to enable adjustment by the liquid level rising member 40 up to the above necessary level is 60 mm. In a case where the sample liquid level does not reach 60 mm, the sample volume is regarded to be insufficient, and analysis of that sample container is omitted while issuing an alarm. In a case where the sample liquid level exceeds 60 mm, the detected signal is delivered to the control unit 51 where the control and data processing deice 19 calculates, .based on the liquid volume necessary for raising the sample liquid level up to 90 mm, the number of pulses applied to a pulse motor by which the liquid level rising member 40 is inserted to the sample container, the calculated number of pulses being stored in a built in storage.

The grounding terminal 39b of the liquid level sensing electrodes has its distal end bent into a scoop shape and also serves as a stirrer 44. For the sample to be analyzed, the stirrer 44 is now moved up and down several times by operating the arm 41 vertically so that the sample liquid is stirred for mixing.

After that, the sample container 20 is advanced by one step for transfer to the dipping position B, and the arm 41 is horizontally retracted by the drive mechanism 42 so that the liquid level rising member 40 is moved to a location just above the sample container 20 in the dipping position. The liquid level rising member 40 is then inserted into the sample container 20 depending on the number of pulses stored in the above step, followed by coming to a standstill there. This insertion of the liquid level rising member 40 causes the sample liquid level to rise up to the level (90 mm) necessary for thorough immersion of the test strip (FIG. 4b).

While keeping the liquid level rising member 40 in the sample container, the test strip handling device 16 is operated to carry the test strip 23 and lower the same into the sample container in the dipping position for dipping into the sample liquid with one end of the test strip grasped by the grip 37 of the arm 35 (FIG. 4c). After immersion for a predetermined period of time, the grip 37 is elevated to lift the test strip 23 out of the sample liquid for transferring it to the test strip setting position C above the measuring device 17. At the time of reaching the setting position C, the handling device 16 releases a test strip 23a, on which color developing reactions have started, from the grip 37 to be ready for a new test strip. Thereafter, the liquid level rising member 40 is lifted out of the sample container 20 and the arm 41 is horizontally moved toward the washing tank 45. The electrodes 39a, 39b and the liquid level rising member 40 are lowered into the washing tank 45 and washed with a cleaning liquid, following by elevation to a standby position for analysis of the next sample.

In the measuring device 17 shown in FIG. 1, rolled paper 46 is used to transport the test strip 23a which has been received from the test strip handling device 16. The rolled paper 46 is let out and wound up by a reeling device 47 at predetermined time intervals, whereby the test strip 23a placed in the setting position C is transported toward a light detecting position E. With such an arrangement, the test strip 23a is positioned at the light detecting position E in a photometer 49 after a certain period of time from the immersion in the sample.

In the photometer 49, a plurality of small-sized optical sensors of reflection type, each of which comprises light sources formed of LEDs emitting rays of light in specific wavelengths corresponding to analytical items, respectively, and light receiving elements formed of silicon photodiodes, are arranged in one-to-one relation to positions for detecting the reagent sections of the test strip 23a so that the intensity of the reflected light from each reagent section colored by the ongoing reaction is measured. The measurement results are supplied to the control unit 51 via an A/D converter 50 for data processing to be indicated on a liquid crystal display and printed by a printer 53.

The analyzing operation in the present apparatus progresses in response to an input entered from a control panel 54. The test strip on which the measurement has been completed is wound up by the reeling device 47 together with the rolled paper. After the completion of certain cycles of the measurement, the rolled paper wound up together with the test strips is removed out of the reeling device and discarded.

Figure 5:
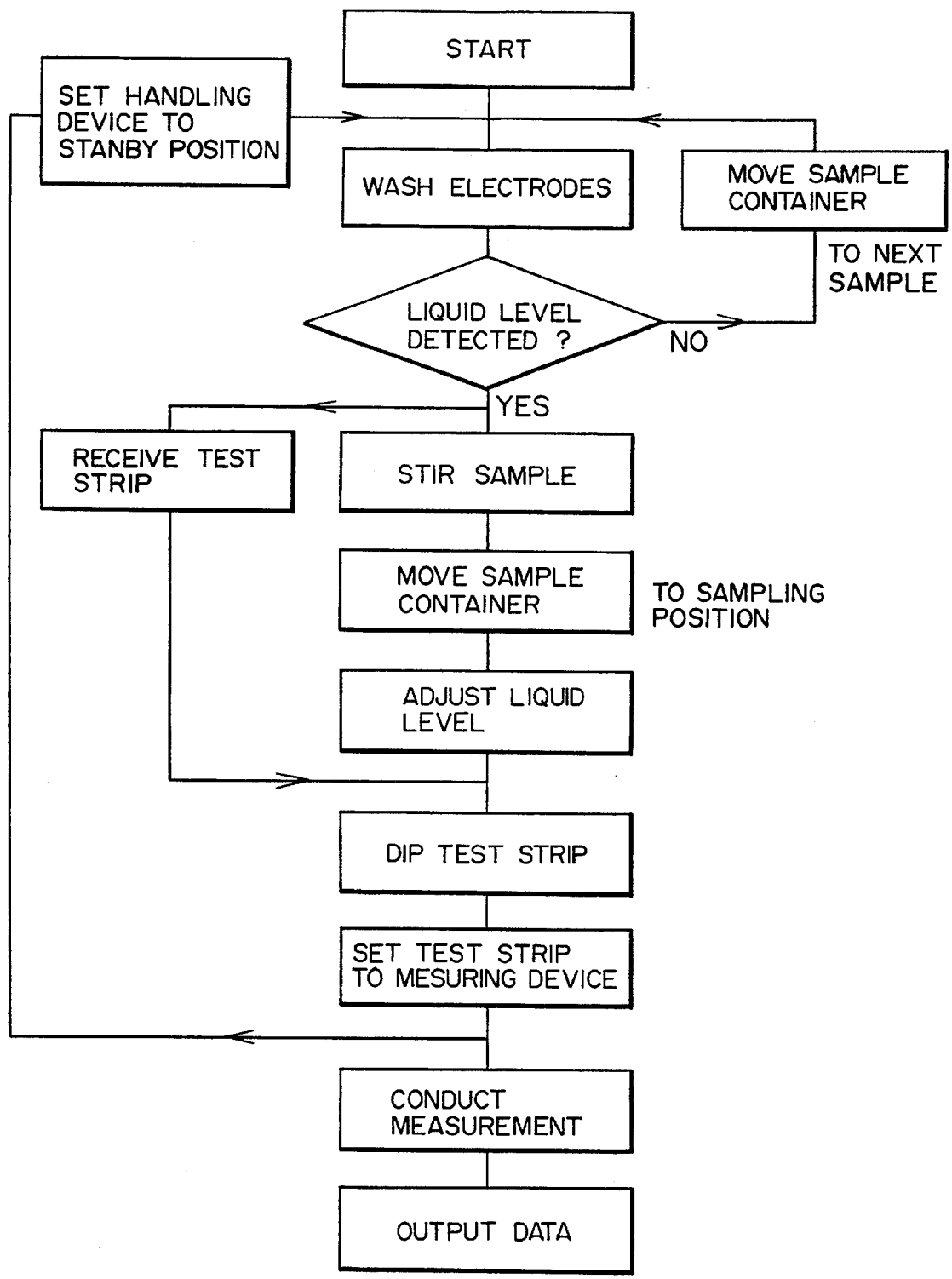
FIG. 5 is a flowchart showing operations of the analyzer shown in FIG. 1.

FIG. 5 shows a flowchart of a program example for steps of analyzing an operation performed in the analyzer of FIG. 1. The analyzing operation is started in a state that the first one of the sample containers 20 loaded in the sample positioning device 14 is positioned at the liquid level sensing position D. The program for the analyzing operation progresses with each cycle of 12 seconds by repeated operations of "washing the electrodes", "dipping the test strip" and "setting the test strip in the light detecting position", during which the test strips are successively dipped into samples on the turntable of the sample positioning device 14 and transferred to the measuring device 17. The test strips 23a transferred to the measuring device 17 are transported with a cycle of 12 seconds such that each test strip is positioned at the light detecting position E after 60 seconds from the dipping and measured by the photometer 49 which outputs the measurement result. In other words, with this program, the result of analysis on the reaction developing for 60 seconds after the dipping into the sample is obtained at a processing rate of 12 seconds for each sample.

According to the above-explained embodiment, when the sample liquid level in the sample container is short of the level necessary for thoroughly immersing the test strip in the sample, the sample liquid level can be raised up to the level necessary for thorough immersion of the test strip. Therefore, even in the foregoing case of using a test strip which has a long test region corresponding to many analytical items, it is possible to conduct analysis with a relatively small volume of the sample liquid to be prepared in the sample container, which is easy to handle.

With the increased number of items to be checked in clinical examinations, in a screening test of urine which uses test strips capable of color developing reactions, there has been employed such a test strip for multi-item analysis as including 10 or more test items. When loading those test strips on an automatic analyzer, it is troublesome and poses nerve strain for an operator to prepare numerous sample containers beforehand so that each container contains a sample liquid with its surface level enabling all reagent sections on the test strip to be thoroughly immersed in the sample liquid. However, the embodiment shown in FIG. 1 allows the operator to sample a volume of the sample liquid, which is relatively small and thus easy to handle, in each sample container. Additionally, even if the volume of the sample liquid is sampled in a rough manner, the sample liquid level can always be adjusted in the course of measurement to a height sufficient to thoroughly immerse all the reagent sections on the test strip in the sample liquid.

Figure 6:
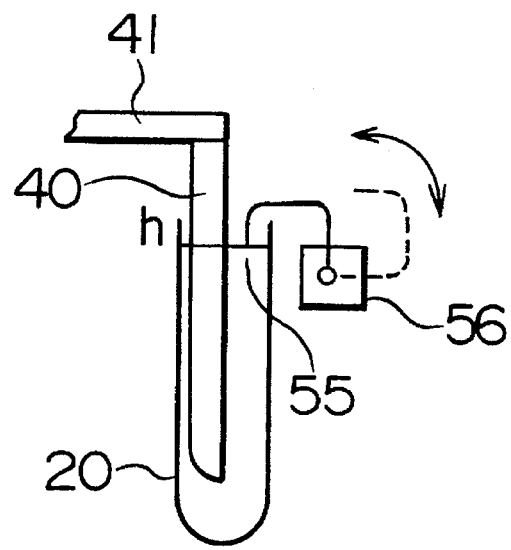
FIG. 6 is a schematic view for explaining a principal part of another embodiment of the present invention.

A second embodiment according to the present invention will next be described with reference to FIG. 6. FIG. 6 shows an arrangement only in the vicinity of the test strip dipping position B. The remaining arrangement is the same as that for the analyzer of FIG. 1. This second embodiment includes a liquid level sensor for sensing the liquid at a predetermined position that must be reached for thorough immersion of the test strip. According to a method of the second embodiment, the sensor detects that the sample liquid level raised by inserting the liquid level rising member 40 into the sample container 20 has reached the predetermined position, whereupon the insertion of the liquid level rising member 40 is stopped. The detecting operation is performed in the same step as when the liquid level rising member 40 is inserted. More specifically, the sensor comprises a pair of electrodes 55 and 40 (i.e., one electrode 55 the liquid level rising member). The electrode 55 is arranged such that it can be rotated to enter the sample container 20 by a drive mechanism 56 for rotating the electrode 55 independently of the liquid level rising member 40, and is positioned to a level position h corresponding to the sample liquid level necessary for immersion of the test strip.

The liquid level rising member 40 is formed of conductive material and serves also as a negative electrode. With the electrode 55 thus positioned, the liquid level rising member 40 is inserted in the sample container to raise the sample liquid level until the electrode pair detects that the sample liquid level has reached the level position h of the positive electrode 55. The insertion of the liquid level rising member 40 is stopped in response to a detection signal, thereby providing the predetermined sample liquid level. In comparison with the method of FIG. 4, the method of this embodiment has a feature capable of directly detecting the fact that the sample liquid level has reached the predetermined level position. To realize this feature, however, it is required to operate the electrode drive mechanism 56 independently of the liquid level rising member, and also to carefully position the positive electrode and the electrode drive mechanism to avoid interference with the dipping of the test strip.

Figure 7:
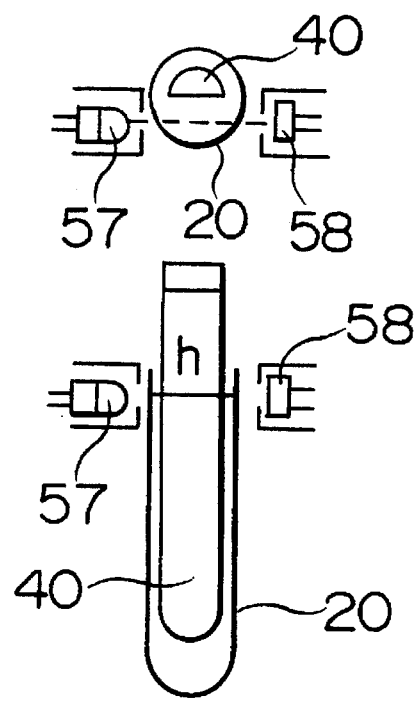
FIG. 7 is a schematic view for explaining a principal part of a further embodiment of the present invention.

A third embodiment according to the present invention will next be described with reference to FIG. 7. The embodiment of FIG. 7 employs optical means as a liquid level sensor. In FIG. 7, there are shown a schematic plan view in the upper side and a schematic side view in the lower side. A small-sized optical sensor which comprises a light source formed of an LED and a light receiving element formed of a silicon photodiode, is provided at a level position h corresponding to the predetermined sample liquid level in the dipping position, thereby detecting arrival of the sample liquid level to the predetermined level for control of the extent by which the liquid level rising member 40 is inserted into the sample container 20. If a ray of light is emitted to pass the center of the sample container 20, the liquid level rising member 40 would interfere with the light path. For this reason, the arrangement is made to offset the ray of light from the center of the sample container as shown. The presence of the sample causes the light path to bend due to refraction upon entering and exiting out of the sample, so that the magnitude of a signal from the sensor is reduced. By utilizing such a signal change, rising of the sample up to the predetermined level is detected.

It should be noted that the present invention is not limited to the embodiments mentioned above. By way of example, the sample positioning device may be arranged to move a rack, instead of the turntable 21, for transporting samples. Also, the test strip handling device 16 may be arranged to drive the arm by moving it linearly rather than rotatively or swingably. Other various mechanical transporting means than using the rolled paper may also be adopted to transport the test strips in the measuring device 17. In place of the photometer in which a plurality of sensors are provided corresponding to the individual analytical items as illustrated in the embodiment, it is further possible to carry out optical measurement while scanning the reagent sections on the test strip, by using a photometer which has detects light having a plurality of wavelengths.

What is claimed is:

1. In an analytical apparatus wherein a test strip is dipped into and lifted out of a sample liquid and then transferred to a reaction measuring device where reagent sections on the test strip are measured, the improvement comprising:

a liquid level rising member;

a sample positioning device for successively positioning sample containers containing the sample liquid at a test strip dipping position, each of the sample containers being open at an upper end thereof for receiving the liquid level rising member and the test strip;

a liquid level adjustment device for inserting the liquid level rising member into the sample liquid in the sample container located at the test strip dipping position to displace a volume of the sample and change the effective volume thereof to a predetermined volume in accordance with characteristics of the test strip, and for removing the liquid level rising member from the sample liquid; and a test strip handling device for dipping a test strip with reagent sections formed thereon into the sample liquid in the sample container located at the test strip dipping position while said liquid level rising member is kept inserted in said sample container by said liquid level adjustment device at said test strip dipping position;

wherein the liquid level adjustment device, when inserted in the sample liquid, enables a greater portion of the test strip to contact the sample liquid upon immersion of the test strip in the sample liquid as compared to a portion of the test strip that would contact the sample liquid absent sample volume displacement by the liquid level rising member.

2. An analytical apparatus according to claim 1, wherein said liquid level adjustment device moves said liquid level rising member to sufficiently displace an amount of sample liquid in said sample container so that all reagent sections on said test strip contact the sample.

3. An analytical apparatus according to claim 1, further comprising liquid level sensing means for determining the extent by which said liquid level rising member should be inserted into the sample container.

4. An analytical apparatus according to claim 1, further comprising liquid level sensing means for determining the level of said sample liquid in said sample containers, wherein the liquid level adjustment device moves the liquid level rising member into the sample liquid in accordance with the level sensed by the liquid level sensing means.

5. In an analytical apparatus that includes a sample positioning device for positioning sample containers, each sample container being open at an upper end thereof and containing a sample liquid, to a predetermined position, and a test strip handling device for dipping a test strip with reagent sections formed thereon into the sample liquid in the sample container located at said predetermined position and then transferring the test strip to a reaction measuring device, the improvement comprising:

a liquid level rising member;

a liquid level adjustment device for inserting the liquid level rising member into said sample container located at said predetermined position to displace a volume of the sample liquid and raise a level of said sample liquid in said sample container to a predetermined level based on characteristics of the test strip, and for removing the liquid level rising member from the sample liquid;

wherein the test strip handling device dips the test strip into the sample liquid while said liquid level rising member is kept inserted in said sample container by said liquid level adjustment device at said predetermined position.

6. An analytical apparatus according to claim 5, wherein said liquid level rising member comprises a vertically-movable rod member shaped to conform to an inner wall of said sample container.

7. An analytical apparatus according to claim 5, wherein the liquid level rising member displaces a volume of sample liquid sufficient to permit all test strip reagent sections to be immersed in the sample liquid when the liquid level rising member is immersed in the sample.

8. An analytical apparatus according to claim 5, further comprising liquid level sensing means for detecting the sample liquid level in said sample container, wherein the depth by which said liquid level rising member should be inserted to said sample container is controlled based on a signal from said liquid level sensing means indicating said predetermined level.

9. An analytical method according to claim 8, wherein the liquid level sensing means includes an electrode set at a predetermined depth inside the sample container so that the signal is output from the liquid level sensing means when the sample contacts the electrode.

10. An analytical apparatus according to claim 8, wherein the liquid level sensing means includes means for optically sensing when the sample liquid level surface reaches said predetermined level in the one sample container, and for outputting the signal when the sample liquid level surface reaches the reference level.

11. An analytical apparatus for analyzing, by test strip immersion, liquid samples contained in sample containers successively positioned at a predetermined position, comprising:

a liquid level rising member;

a liquid level adjustment device for reducing the effective volume of an open end sample container containing a sample liquid by inserting the liquid level rising member into said sample container through said open end prior to test strip immersion to raise a surface level of the sample liquid to a predetermined level based on characteristics of the test strip, and for removing the liquid level rising member from the sample container after test strip immersion; and a test strip handling device for test strip immersion that immerses a test strip having reagent sections formed thereon into the sample liquid in said sample container at said predetermined position while said liquid level rising member is kept inserted in said sample container by said liquid level adjustable device.

12. In an analytical method employing test strips each of which has a plurality of reagent sections for developing colors upon being dipped into a sample liquid in sample containers having an open upper end thereof, said reagent sections being then subjected to optical measurement for color development, the improvement comprising the steps of successively conveying the sample containers to a test strip dipping position, selectively reducing the effective volume of each of said sample containers containing the sample liquid by inserting a liquid level rising member into the sample liquid to correspondingly raise a surface level of the sample liquid in the sample container including stopping the inserting when the surface level of the sample liquid arrives at a predetermined level based on characteristics of the test strip, dipping said test strip into the sample liquid while the sample liquid level is kept raised at the test strip dipping position, and thereafter removing the liquid level rising member.

13. An analytical method according to claim 12, further comprising the steps of, prior to insertion of said liquid level rising member into said sample container, detecting the surface level of the sample liquid in said sample container, and controlling the depth by which said liquid level rising member should be inserted depending on the detected surface level of the sample liquid.

14. A sample liquid handling method for enabling test strip immersion analysis of the sample liquid, comprising the steps of:

containing the sample liquid in sample containers having an open upper end;

successively transferring the sample containers to a test strip dipping position;

inserting a liquid level rising member into a sample liquid contained in the sample container located at the test strip dipping position to reduce the effective volume thereof in accordance with characteristics of the test strip;

dipping a test strip, having a plurality of reagent sections formed thereon in the direction of strip length, into the sample liquid while the liquid level rising member is still inserted in the sample liquid at said test strip dipping position;

removing said test strip from said sample container located at the test strip dipping position; and thereafter removing said liquid level rising member from said sample container located at the test strip dipping position.

15. A method according to claim 14, further comprising the steps of:

prior to dipping the test strip into the sample container located at the test strap dipping position, determining whether a surface level of the sample liquid in said sample container has reached a predetermined reference level or not; and if the sample liquid level has not reached said predetermined reference level, inserting the liquid level rising member into said sample container to raise the sample liquid level until the sample liquid level reaches said predetermined reference level.

16. An analytical method according to claim 15, further including positioning said sample containers at a liquid level sensing position prior to the test strip dipping position and inserting liquid level sensing electrodes into said sample container located at the test strip dipping position as part of said determining whether the predetermined reference level has been reached.

17. An analytical method according to claim 15, wherein when the sample liquid level does not reach said predetermined reference level even after said liquid level rising member is fully inserted to a predetermined maximum depth, an alarm is issued to give a notice of insufficient volume of the sample liquid.

* * * * *